(12) United States Patent
Min et al.

(10) Patent No.: US 10,398,332 B2
(45) Date of Patent: Sep. 3, 2019

(54) METHODS, SYSTEMS, AND APPARATUS FOR NEURAL SIGNAL DETECTION

(71) Applicant: St. Jude Medical, Inc., St. Paul, MN (US)

(72) Inventors: Xiaoyi Min, Thousand Oaks, CA (US); Stuart Rosenberg, Castaic, CA (US); Gabriel Mouchawar, Valencia, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 218 days.

(21) Appl. No.: 14/503,799

(22) Filed: Oct. 1, 2014

(65) Prior Publication Data
US 2015/0018656 A1    Jan. 15, 2015

Related U.S. Application Data

(62) Division of application No. 13/827,308, filed on Mar. 14, 2013, now Pat. No. 8,876,813.

(51) Int. Cl.
*A61B 5/00* (2006.01)
*A61B 5/04* (2006.01)
*A61N 1/05* (2006.01)
*A61B 18/14* (2006.01)
(Continued)

(52) U.S. Cl.
CPC ...... *A61B 5/04001* (2013.01); *A61B 5/04004* (2013.01); *A61B 5/4836* (2013.01); *A61B 18/12* (2013.01); *A61B 18/1492* (2013.01); *A61N 1/05* (2013.01); *A61B 2018/00267* (2013.01); *A61B 2018/00404* (2013.01); *A61B 2018/00434* (2013.01); *A61B 2018/00511* (2013.01);
(Continued)

(58) Field of Classification Search
CPC ..... A61N 1/36125–36196; A61B 2018/00434; A61B 2018/0044; A61B 2018/00446
USPC .................................................. 600/544–547
See application file for complete search history.

(56) References Cited

U.S. PATENT DOCUMENTS 3,579,138 A   5/1971  Harris et al.
3,650,277 A   3/1972  Sjostrand et al.
(Continued)

FOREIGN PATENT DOCUMENTS

EP   0835634 A1   4/1998
EP   1166715      1/2002
(Continued)

OTHER PUBLICATIONS

Rippy, Marian K. et al, Catheter-Based Renal Sympathetic Denervation: Chronic Preclinical Evidence for Renal Artery Safety, Clin Res Cardiol (2011) 100:1095-1101.
(Continued)

*Primary Examiner* — Adam J Eiseman
(74) *Attorney, Agent, or Firm* — Armstrong Teasdale LLP

(57) ABSTRACT

Methods, systems, and apparatus for signal detection are described. In one example, a detection assembly includes a signal detector. The signal detector is configured to receive a sensor signal having a peak magnitude and a first frequency and generate an output signal having a magnitude proportional to the peak magnitude of the sensor signal and having a second frequency less than the first frequency of the sensor signal.

16 Claims, 7 Drawing Sheets

(51) Int. Cl.
*A61B 18/12* (2006.01)
*A61B 18/00* (2006.01)

(52) U.S. Cl.
CPC ............... *A61B 2018/00577* (2013.01); *A61B 2018/00839* (2013.01)

(56) References Cited

U.S. PATENT DOCUMENTS

| | | | |
|---|---|---|---|
| 3,909,700 A * | 9/1975 | Ferro | H01L 27/0664 |
| | | | 257/E27.022 |
| 4,240,442 A | 12/1980 | Andresen et al. | |
| 4,254,779 A * | 3/1981 | Miyata | A61B 5/201 |
| | | | 600/544 |
| 4,658,819 A | 4/1987 | Harris et al. | |
| 5,035,694 A | 7/1991 | Kasprzyk et al. | |
| 5,255,679 A | 10/1993 | Imran | |
| 5,300,068 A | 4/1994 | Rosar et al. | |
| 5,357,956 A | 10/1994 | Nardella | |
| 5,365,783 A * | 11/1994 | Zweifel | G01F 23/266 |
| | | | 324/662 |
| 5,368,591 A | 11/1994 | Lennox et al. | |
| 5,387,233 A | 2/1995 | Alferness et al. | |
| 5,465,717 A | 11/1995 | Imran et al. | |
| 5,531,779 A | 7/1996 | Dahl et al. | |
| 5,598,848 A | 2/1997 | Swanson et al. | |
| 5,607,462 A | 3/1997 | Imran | |
| 5,628,313 A | 5/1997 | Webster, Jr. | |
| 5,676,662 A | 10/1997 | Fleischhacker et al. | |
| 5,707,400 A | 1/1998 | Terry, Jr. et al. | |
| 5,769,077 A | 6/1998 | Lindegren | |
| 5,772,590 A | 6/1998 | Webster, Jr. | |
| 5,876,336 A * | 3/1999 | Swanson | A61N 1/06 |
| | | | 600/374 |
| 5,893,885 A | 4/1999 | Webster, Jr. | |
| 5,897,553 A | 4/1999 | Mulier et al. | |
| 5,954,649 A | 9/1999 | Chia et al. | |
| 5,954,719 A | 9/1999 | Chen et al. | |
| 6,004,269 A | 12/1999 | Crowley et al. | |
| 6,012,457 A | 1/2000 | Lesh | |
| 6,016,437 A | 1/2000 | Tu et al. | |
| 6,024,740 A | 2/2000 | Lesh et al. | |
| 6,073,048 A | 6/2000 | Kieval et al. | |
| 6,096,037 A | 8/2000 | Mulier et al. | |
| 6,117,101 A | 9/2000 | Diederich et al. | |
| 6,161,543 A | 12/2000 | Cox et al. | |
| 6,178,349 B1 | 1/2001 | Kieval | |
| 6,200,312 B1 | 3/2001 | Zikorus et al. | |
| 6,216,044 B1 | 4/2001 | Kordis | |
| 6,233,491 B1 | 5/2001 | Kordis et al. | |
| 6,283,951 B1 | 9/2001 | Flaherty et al. | |
| 6,287,608 B1 | 9/2001 | Levin et al. | |
| 6,292,695 B1 | 9/2001 | Webster, Jr. et al. | |
| 6,322,559 B1 | 11/2001 | Daulton et al. | |
| 6,421,558 B1 * | 7/2002 | Huey | A61B 5/04882 |
| | | | 600/546 |
| 6,460,545 B2 | 10/2002 | Kordis | |
| 6,522,926 B1 | 2/2003 | Kieval et al. | |
| 6,613,045 B1 | 9/2003 | Laufer et al. | |
| 6,616,624 B1 | 9/2003 | Kieval | |
| 6,635,054 B2 | 10/2003 | Fjield et al. | |
| 6,656,174 B1 | 12/2003 | Hedge et al. | |
| 6,669,655 B1 | 12/2003 | Acker et al. | |
| 6,699,231 B1 | 3/2004 | Sterman et al. | |
| 6,748,255 B2 | 6/2004 | Fuimaono et al. | |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,653,438 B2 | 1/2010 | Deem et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 | 1/2013 | Demarais et al. | |
| 8,442,639 B2 | 5/2013 | Walker et al. | |
| 8,454,594 B2 | 6/2013 | Demarais et al. | |
| 8,545,495 B2 | 10/2013 | Scheib | |
| 9,022,948 B2 | 5/2015 | Wang | |
| 2002/0068885 A1 | 6/2002 | Harhen et al. | |
| 2002/0120304 A1 | 8/2002 | Mest | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0215186 A1 | 10/2004 | Cornelius et al. | |
| 2004/0249302 A1 * | 12/2004 | Donoghue | A61B 5/04001 |
| | | | 600/544 |
| 2005/0288730 A1 | 12/2005 | Deem et al. | |
| 2006/0089678 A1 | 4/2006 | Shalev | |
| 2007/0135875 A1 | 6/2007 | Demarais et al. | |
| 2008/0255478 A1 | 10/2008 | Burdette | |
| 2009/0076409 A1 | 3/2009 | Wu et al. | |
| 2010/0016762 A1 | 1/2010 | Thapliyal et al. | |
| 2010/0094209 A1 | 4/2010 | Drasler et al. | |
| 2010/0156852 A1 * | 6/2010 | Chu | G06F 3/0418 |
| | | | 345/176 |
| 2010/0168737 A1 | 7/2010 | Grunewald | |
| 2010/0210958 A1 | 8/2010 | Manwaring et al. | |
| 2010/0249773 A1 | 9/2010 | Clark et al. | |
| 2010/0268307 A1 | 10/2010 | Demarais et al. | |
| 2010/0286684 A1 | 11/2010 | Hata et al. | |
| 2011/0004087 A1 | 1/2011 | Fish et al. | |
| 2011/0118726 A1 | 5/2011 | de la Rama et al. | |
| 2011/0137298 A1 | 6/2011 | Nguyen et al. | |
| 2011/0160720 A1 | 6/2011 | Johnson | |
| 2011/0213231 A1 | 9/2011 | Hall et al. | |
| 2011/0257641 A1 | 10/2011 | Hastings et al. | |
| 2011/0264011 A1 | 10/2011 | Wu et al. | |
| 2011/0264086 A1 | 10/2011 | Ingle | |
| 2012/0143097 A1 | 6/2012 | Pike, Jr. | |
| 2012/0143298 A1 | 6/2012 | Just et al. | |
| 2012/0296232 A1 | 11/2012 | Ng | |
| 2012/0323233 A1 | 12/2012 | Maguire et al. | |
| 2013/0116737 A1 | 5/2013 | Edwards et al. | |
| 2013/0131743 A1 | 5/2013 | Yamasaki et al. | |
| 2013/0144251 A1 | 6/2013 | Sobotka | |
| 2013/0172715 A1 | 7/2013 | Just et al. | |

FOREIGN PATENT DOCUMENTS

| | | |
|---|---|---|
| EP | 2264828 A1 | 12/2010 |
| GB | 2016708 | 9/1979 |
| WO | 97/45157 | 12/1997 |
| WO | 00/66020 | 11/2000 |
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |

(56) References Cited

FOREIGN PATENT DOCUMENTS

| WO | 2012/064818 | 5/2012 |
|---|---|---|
| WO | 2012/106492 | 8/2012 |

OTHER PUBLICATIONS

Ritz, Eberhard, New Approaches to Pathogenesis and Management of Hypertension, Clin J Am Soc Nephrol 4: 1886-1891, 2009.
Robbins, Ivan M. et al, Pulmonary Vein Stenosis After Catheter Ablation of Atrial Fibrillation, Circulation Journal of the American Heart Association, 1998;98:1769-1775.
Rocha-Singh, Krishna J., Catheter-Based Sympathetic Renal Denervation a Novel Strategy for the Treatment of Resistant Hypertension, Endovascular Today, Aug. 2009, 52-56.
Rocha-Singh, Krishna J. Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of the American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of the American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of the American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of the American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.—Theory and Practice, Ag(SUPPL.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.

(56) References Cited

OTHER PUBLICATIONS

Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages.
Wyss, J.M. et al, Sensory Denervation of the Kidney Attenuates Renovascular Hypertension in the Rat, Am J Physiol Heart Circ Physiol 250:H82-H86, 1986.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Izzo, Jr, Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.
Labeit, Alexander Michael et al, Changes in the Prevalence, Treatment and Control of Hypertension in Germany? A Clinical-

(56) References Cited

OTHER PUBLICATIONS

Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After Symplicity HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of the American Heart Association, 1999, 34:724-728.
Mcgahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal but Not Cardiac Sympathetic Activity in Humans; Hypertension Journal of The American Heart Association, 1991;18:575-582.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, Time Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al. The Effects of Renal Denervation on Patients Suffering from Nephritis, J Clin Invest. 1935;14 (4):443-458.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.

(56) References Cited

OTHER PUBLICATIONS

Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of the American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis a Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic

(56) References Cited

OTHER PUBLICATIONS

Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:I-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.
Howard, James P. et al, Size of Blood Pressure Reduction from Renal Denervation: Insights from Meta-Analysis of Antihypertensive Drug Trials of 4121 Patients with Focus on Trial Design: the Converge Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, (2013) 0: 1-8.
Huang, Shoei K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of The American Heart Association, 1998;32:249-254.
Humpreys, Michael H., Renal Nerves and CKD: Is Renal Denervation the Answer?, Journal of The American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Zazgornik, Jan et al, Bilateral Nephrectomy: The Best, but Often Overlooked, Treatment for Refractory Hypertension in Hemodialysis Patients, AJH 1998; 11:1364-1370.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
International Search Report and Written Opinion for Application No. PCT/US2014/019466 dated Sep. 9, 2014.
Horiuchi, T K et al: "A low-pwer CMOS neural amplifier with amplitude measurements for spike sorting", Proceedings/2004 IEEE International Symposium on Circuits and Systems: May 23-26, 2004, Sheraton Vancouver Wall Centre Hotel, Vancouver, British Columbia, Canada, IEEE Operations Center, Piscataway, NJ, May 23, 2004 (May 23, 2004), pp. 29-32, XP010719729, ISBN:978-0-7803-8251-0 abstract; figures 1-10 Introduction, Design Approach; p. 29 Peak-to-Trough Difference; p. 30 Neural Spikes and Sorting; p. 32.
Abboud, Francois M., The Sympathetic System in Hypertension, State-of-the-Art Review, Hypertension Journal of the American Heart Association, Hypertension 4 (suppl II):II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural

(56) References Cited

OTHER PUBLICATIONS

Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.

\* cited by examiner

METHODS, SYSTEMS, AND APPARATUS FOR NEURAL SIGNAL DETECTION

This application is a divisional of application Ser. No. 13/827,308 filed on Mar. 14, 2013, the disclosure of which is expressly incorporated herein by reference.

BACKGROUND OF THE DISCLOSURE a. Field of the Disclosure

The present disclosure relates generally to methods, systems, and apparatus for signal detection. More particularly, the present disclosure relates neural signal detection methods, systems, and apparatus that utilize a circuit to measure and record the amplitude of nerve firings along the spinal cord and peripheral nerves.

b. Background Art

Medical devices and procedures that affect or involve neural signals are known. It is known, for example, that ablation systems are used to perform ablation procedures to treat certain conditions of a patient. A patient experiencing arrhythmia, for example, may benefit from cardiac ablation to prevent irregular heartbeats caused by arrhythmogenic electric signals generated in cardiac tissues. By ablating or altering cardiac tissues that generate such unintended electrical signals, the irregular heartbeats may be stopped. Ablation systems are also known for use in treating hypertension, and in particular drug-resistant hypertension, in patients. In particular, renal ablation systems, also referred to as renal denervation systems, are used to create lesions along the renal sympathetic nerves, which are a network of nerves in the renal arteries that help control and regulate blood pressure. The intentional disruption of the nerve supply has been found to cause blood pressure to decrease. Other medical devices that measure or record neural signals include, spinal cord stimulation (SCS) systems that provide pulsed electrical stimulation to a patient's spinal cord to control chronic pain, and cardiac rhythm management devices (CRMD) used to regulate a patient's heart beat.

Known techniques for detecting high frequency signals in a body, and particularly high frequency neural signals, typically require very sensitive equipment, as nerve signals differ from cardiac signals and are at a higher frequency and much narrower pulse duration. In particular, neural signals are typically collected through surgically positioned microelectrodes or micropipette electrodes. The signals generated by these sensors are generally sampled by controllers at a sampling rate of about four kilohertz. The sensors and controllers required for such techniques are not inexpensive. Moreover, some medical devices and procedures may benefit from limited information about neural signals and do not require the detailed information that is obtained using the known techniques.

There is a need, therefore, for neural signal detection systems that do not require expensive, surgically implanted electrodes, utilize simpler and less expensive controllers with relatively low sampling rates, and provide useful data about detected neural signals in real time. It would also be beneficial if the neural signal detection systems were compact in size so that they could be easily built into or onto an ablation catheter, or into or onto an implantable medical device such as a spinal cord stimulator device or a cardiac rhythm management device.

BRIEF SUMMARY OF THE DISCLOSURE

In one aspect, a neural signal detector includes a rectifier circuit and a peak detector circuit operatively connected to the rectifier circuit. The rectifier circuit is configured to receive a time varying neural signal from a neural sensor and output a rectified signal corresponding to the received signal. The rectifier circuit is configured to receive the rectified signal and to provide an output signal proportional to a peak magnitude of the rectified signal.

In another aspect, a detection assembly includes a signal detector. The signal detector is configured to receive a sensor signal having a peak magnitude and a first frequency and generate an output signal having a magnitude proportional to the peak magnitude of the sensor signal and having a second frequency less than the first frequency of the sensor signal.

Another aspect of the present disclosure is an ablation system. The ablation system includes a signal detector and a controller. The signal detector is configured to receive, from a neural sensor, a plurality of signals and generate a pre-ablation output signal having a first magnitude proportional to a peak magnitude of at least one pre-ablation signal of the plurality of signals and having a duration greater than said at least one pre-ablation signal of the plurality of signals. The controller is operatively coupled to the signal detector to sample the pre-ablation output signal.

Another aspect of the present disclosure is an ablation catheter comprising an ablation electrode, a sensing electrode, and a neural signal detector operatively connected to the sensing electrode. The neural signal detector comprises a rectifier circuit configured to receive a time varying neural signal from a neural sensor and output a rectified signal corresponding to the received signal and a peak detector circuit operatively connected to the rectifier circuit to receive the rectified signal and configured to provide an output signal proportional to a peak magnitude of the rectified signal.

Another aspect of the present disclosure is a spinal cord stimulation device comprising an implantable stimulating electrode, a sensing electrode, and a neural signal detector operatively connected to the sensing electrode. The neural signal detector comprises a rectifier circuit configured to receive a time varying neural signal from a neural sensor and output a rectified signal corresponding to the received signal and a peak detector circuit operatively connected to the rectifier circuit to receive the rectified signal and configured to provide an output signal proportional to a peak magnitude of the rectified signal.

Another aspect of the present disclosure is a cardiac rhythm management device comprising a pacing lead, a sensing electrode, and a neural signal detector operatively connected to the sensing electrode. The neural signal detector comprises a rectifier circuit configured to receive a time varying neural signal from a neural sensor and output a rectified signal corresponding to the received signal and a peak detector circuit operatively connected to the rectifier circuit to receive the rectified signal and configured to provide an output signal proportional to a peak magnitude of the rectified signal. The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the drawings.

DETAILED DESCRIPTION OF THE DISCLOSURE

The present disclosure is generally directed to methods and systems for measuring and/or recording neural signals along the spinal cord or in peripheral nerves, including cardiac nerves and renal nerves. The methods and systems described herein measure and/or record the amplitude of neural signals. The systems of the present disclosure utilize a small-sized circuit that includes generally a high frequency diode, a capacitor, and a resistor as a demodulator as described herein. In many cases, the circuitry can be sized and configured to fit inside of a medical device or on a lead or catheter. The circuitry for measuring and/or recording the activities of nerves as described herein may be particularly useful for cardiac and renal ablation procedures, as well as for numerous implantable medical devices as described herein.

This approach may allow an ablation catheter system to measure the success of renal efferent and afferent nerve ablation during a renal denervation procedure to provide immediate success feedback to a doctor throughout an ablation procedure. Further, this approach may allow for spinal cord stimulator devices to provide improved sensing capabilities. Still further, this approach to measuring nerve amplitude may enable responses from interventions between neuro and cardiac rhythm management devices such as the recording of nerve responses from stimulating different sites of T1-T5 and T11-L2 in the spinal cord or sites along the sternum and intracardiac sites. These and other benefits of the disclosure are set forth in detail herein.

Figure 1:
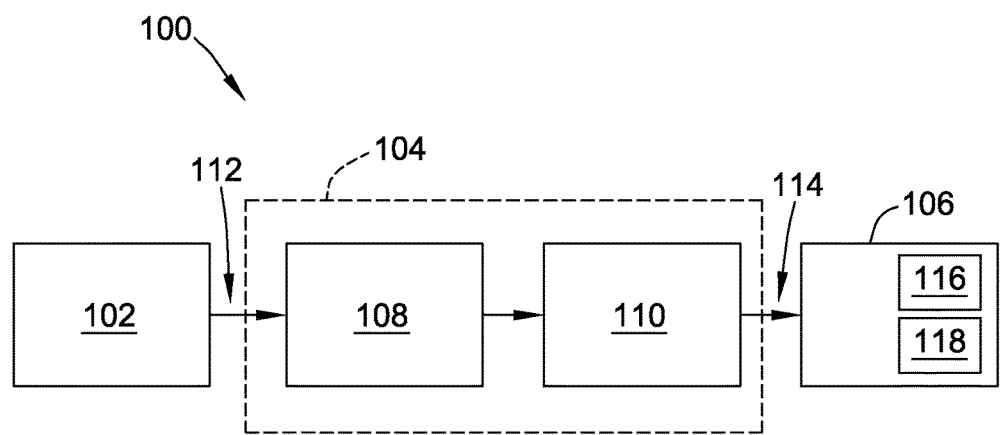
FIG. 1 is a block diagram of one embodiment of a signal detection assembly.

Referring now to the drawings and in particular to FIG. 1, detection assembly 100, includes sensor 102, signal detector 104, and controller 106. Sensor 102 is operable to detect a signal and generate a sensor signal proportional to the detected signal. Sensor 102 is operatively coupled to Signal detector 104. Signal detector 104 receives the sensor signal from sensor 102 and generates an output signal proportional to the sensor signal. Controller 106 is coupled to signal detector 104 to receive the output signal from signal detector 104.

In the exemplary embodiment, signal detector 104 is configured to generate an output signal having characteristics, such as magnitude, frequency, etc., that controller 106 is operable to sample. In particular, the received signal has a peak magnitude and a first frequency. Signal detector 104 generates an output signal with a magnitude that is proportional to the peak magnitude at a second frequency that is less than the first frequency. In the illustrated embodiment, signal detector 104 generates an output signal with a magnitude that is substantially equal to the peak magnitude of the sensor signal. In other suitable embodiments, signal detector 104 generates an output signal with a magnitude that is greater or lesser than, but proportional to, the peak magnitude of the sensor signal. Thus, controller 106, which may have a sampling resolution too low for accurate sampling of the sensor signal, is provided with the output signal by signal detector 104, at a frequency, the second frequency, that it may accurately sample.

Referring again to FIG. 1, signal detector 104 includes rectifier circuit 108 and peak detector circuit 110. Rectifier circuit 108 receives the sensor signal, which is a time varying signal and may be an alternating current (AC) signal, at input 112 from sensor 102. Rectifier circuit 108 rectifies the received sensor signal and outputs a rectified signal to peak detector circuit 110. Peak detector circuit 110 detects the peak magnitude of the rectified signal and generates an output signal with a magnitude proportional to the peak magnitude of the rectified signal and the sensor signal at a frequency less than the frequency of the sensor signal. The output signal is output from peak detector circuit 110 and signal detector 104 via output 114. Rectifier circuit 108 and peak detector circuit 110 may include any circuits and/or components suitable for operation as described herein. Some exemplary rectifier circuits suitable for use as rectifier circuit 108 and some exemplary peak detector circuits suitable for use as peak detector circuit 110 are described in detail below.

The illustrated controller 106 includes processor 116 and memory device 118 coupled to processor 116. Other suitable embodiments do not include processor 116 and/or memory device 118. The term "processor" refers herein generally to any programmable system including systems and microcontrollers, reduced instruction set circuits (RISC), application specific integrated circuits (ASIC), programmable logic circuits, field programmable gate array (FPGA), gate array logic (GAL), programmable array logic (PAL), digital signal processor (DSP), and any other circuit or processor capable of executing the functions described herein. The above examples are exemplary only, and thus are not intended to limit in any way the definition and/or meaning of the term "processor." Although a single processor is illustrated in FIG. 1, processor 116 may include more than one processor and the actions described herein may be shared by more than one processor. Moreover, although controller 106 is illustrated in FIG. 1 as a component of detection assembly 100, controller 106 may be a part of and/or shared with another system, such as a system with which detection assembly 100 is used.

Memory device 118 stores program code and instructions, executable by processor 116. When executed by processor 116, the program code and instructions cause processor 116 to operate as described herein. Memory device 118 may include, but is not limited to only include, non-volatile RAM (NVRAM), magnetic RAM (MRAM), ferroelectric RAM (FeRAM), read only memory (ROM), flash memory and/or Electrically Erasable Programmable Read Only Memory (EEPROM). Any other suitable magnetic, optical and/or semiconductor memory, by itself or in combination with other forms of memory, may be included in memory device 118. Memory device 118 may also be, or include, a detachable or removable memory, including, but not limited to, a suitable cartridge, disk, CD ROM, DVD or USB memory. Although illustrated separately from processor 116, memory device 118 may be integrated with processor 116 in other suitable embodiments.

Figure 2:
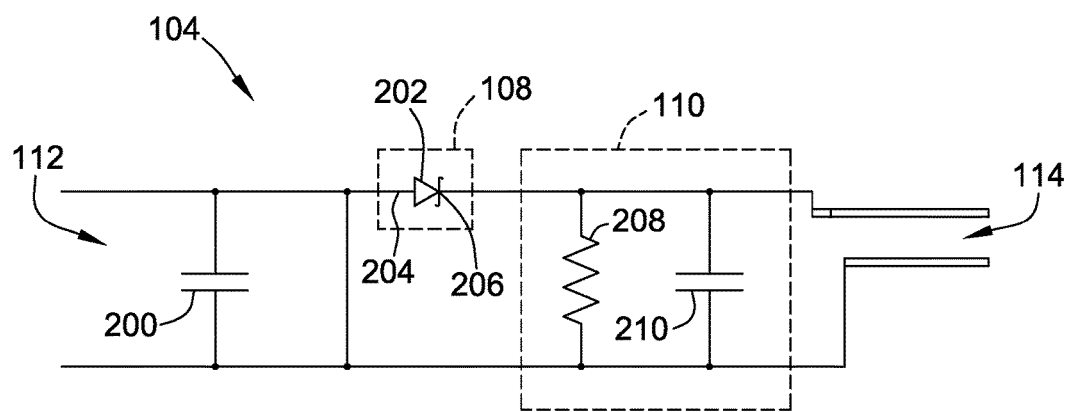
FIG. 2 is a simplified schematic of one example signal detector for use in the detection assembly shown in FIG. 1.

FIG. 2 is a schematic diagram of an exemplary embodiment of signal detector 104 with a passive rectifier circuit 108 and passive peak detector circuit 110. In the signal detector shown in FIG. 2, input 112 is configured for connection to bipolar sensor 102 (not shown). In other embodiments, input 112 may be configured for connection to any other suitable type of sensor 102 including, for example, a unipolar sensor 102. A feed-through capacitor 200 is coupled to input 112 to pass the sensor signal to passive rectifier circuit 108. In other suitable embodiments, feed-through capacitor 200 is not included in signal detector 104.

Passive rectifier circuit 108 in FIG. 2 is a positive half-wave rectifier circuit. In other suitable embodiments, passive rectifier circuit 108 may be any other suitable passive rectifier circuit including, for example, a full wave rectifier circuit, a negative half wave rectifier circuit, etc. Passive rectifier circuit 108 includes diode 202. Diode 202 includes anode 204 and cathode 206. Generally, diode 202 conducts current when it is forward biased, i.e., when a bias voltage exceeding a positive threshold voltage differential is applied across diode 202 from anode 204 to cathode 206. Diode 202 blocks current when it is reverse biased, i.e., when a bias voltage that does not exceed the positive threshold voltage differential is applied across diode 202 from anode 204 to cathode 206. In FIG. 2, diode 202 may be a Schottky diode with a relatively low threshold voltage, also referred to as a diode forward voltage drop, between about 0.2 volts and 0.4 volts. In other suitable embodiments, diode 202 is any other suitable type of diode with a relatively low threshold voltage (e.g., less than about 0.5 volts). In some embodiments, diode 202 is a germanium diode. When diode 202 is forward biased, current, e.g., the sensor signal, flows through diode 202 to passive peak detector circuit 110. When diode 202 is reverse biased, e.g., when the voltage differential from anode 204 to cathode 206 is less than the threshold voltage, diode 202 prevents current from flowing between the passive rectifier circuit 108 and passive peak detector circuit 110. Thus, only the positive portion of the rectified signal that exceeds the bias voltage is delivered from passive rectifier circuit 108 to passive peak detector circuit 110.

Passive peak detector circuit 110 includes resistor 208 and capacitor 210. Resistor 208 is coupled in parallel with capacitor 210. The voltage across capacitor 210 is, via output 114, the output signal of passive peak detector circuit 110 and signal detector 104. When current is permitted to flow through rectifier circuit 108 to peak detector circuit 110, the voltage on capacitor 210 increases as a function of the time constant, tau ($\tau$), defined by the values of paralleled resistor 208 and capacitor 210. More specifically, the time constant is equal to the capacitance of capacitor 210 multiplied by the resistance of resistor 208. Approximately when the rectified signal reaches a peak value and begins to decrease, diode 202 becomes reversed biased, i.e., the difference between the voltage of the sensor signal applied to anode 204 of diode 202 and the voltage across capacitor 210 is less than the threshold voltage of diode 202. Diode 202 no longer conducts current and the voltage on capacitor 210 is discharged through resistor 208 at a rate defined by the time constant. The resistance of resistor 208 and the capacitance of capacitor 210 are selected to result in a time constant large enough that the voltage on the capacitor will discharge slowly enough for controller 106 to accurately sample the peak voltage on capacitor 210. In one example implementation, controller 106 has a sampling resolution of four milliseconds (ms). It is generally desirable for peak detector circuit 110 to have a time constant greater than the sampling resolution of the controller. Accordingly, in this example, resistor 208 has a resistance of about 200 kiloohms (ku) and capacitor 210 has a capacitance of about 33 nanofarads (nF), resulting in a time constant of about 6.6 ms. To change the time constant to suit a different sampling rate of controller 106, the resistance of resistor 208 and/or the capacitance of capacitor 210 may be suitably varied.

Figure 3:
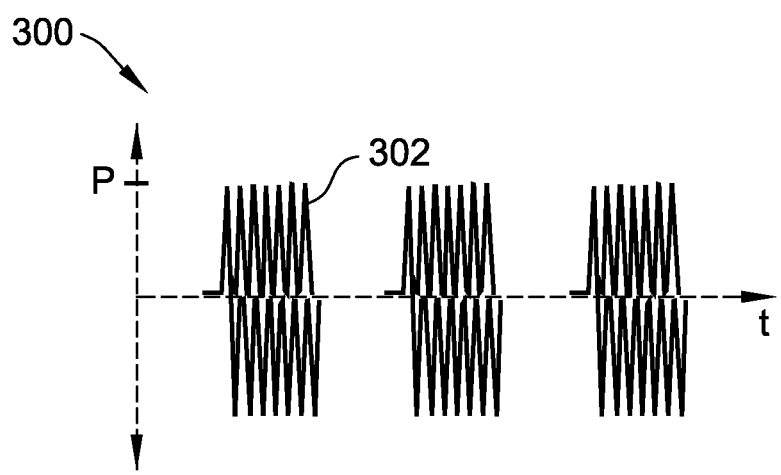
FIG. 3 is a graphical representation of an example input to the signal detector shown in FIG. 2.
Figure 4:
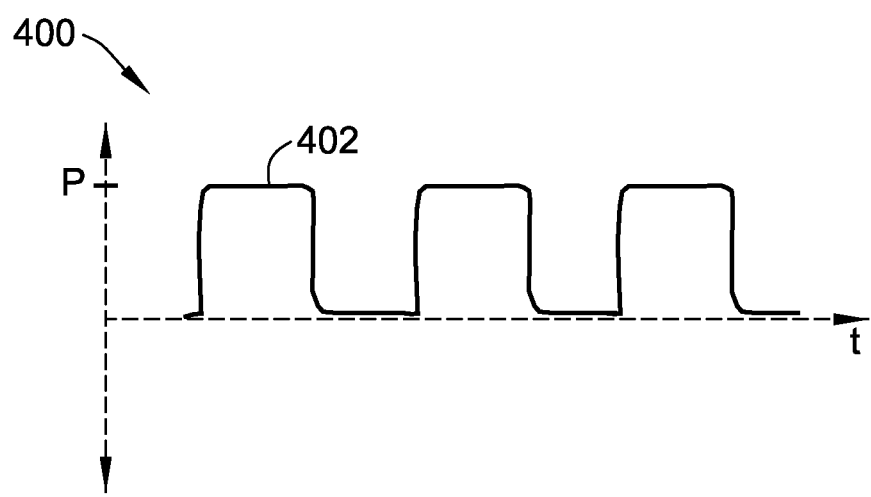
FIG. 4 is a graphical representation of an example output of the signal detector shown in FIG. 2 in response to the input shown in FIG. 3.

A specific example of operation of detection assembly 100 including signal detector 104 as shown in FIG. 2 will be described with reference to FIGS. 3 and 4. For this specific example, a series of pulses of 64 megahertz (MHz) signals were induced on input 112 to simulate a high frequency sensor signal. The 64 MHz signals have a period of about 15.6 nanoseconds (ns). In this example, resistor 208 had a resistance of 30 k$\Omega$ and capacitor 210 had a capacitance of 33 picofarads (pF), resulting in a time constant of about one microsecond ($\mu$s). FIG. 3 is a graph 300 of the magnitude of induced signals 302 as a function of time. Induced signals 302 had a peak magnitude "P". Rectifier circuit 108 rectified induced signals 302 and provided the rectified signals (not shown) to peak detector circuit 110. FIG. 4 is a graph 400 of output signal 402 of peak detector circuit 110, i.e., the voltage on capacitor 210. Capacitor 210 charges up to the peak voltage P of induced signals 302. When the induced signal drops below peak magnitude 302, capacitor 210 begins to discharge through resistor 208. Because the time constant of peak detector circuit 110 is relatively large compared to the period of induced signals 302, the voltage on capacitor 210 does not significantly discharge between signals in each pulse of signals in induced signals 302. Following each pulse of signals of induced signals 302, capacitor 210 discharges to approximately zero volts. As a result, output signal 402 is a square wave with a magnitude of approximately peak magnitude P. The period of square wave output signal 402 is significantly longer than the period of induced signals 302. Put another way, the frequency of output signal 402 is significantly less than the frequency of induced signals 302. Thus, controller 106 may accurately sample output signal 402 at a lower frequency and a lower sampling rate than the frequency and sampling rate that would be required to accurately sample induced signals 302.

Figure 5:
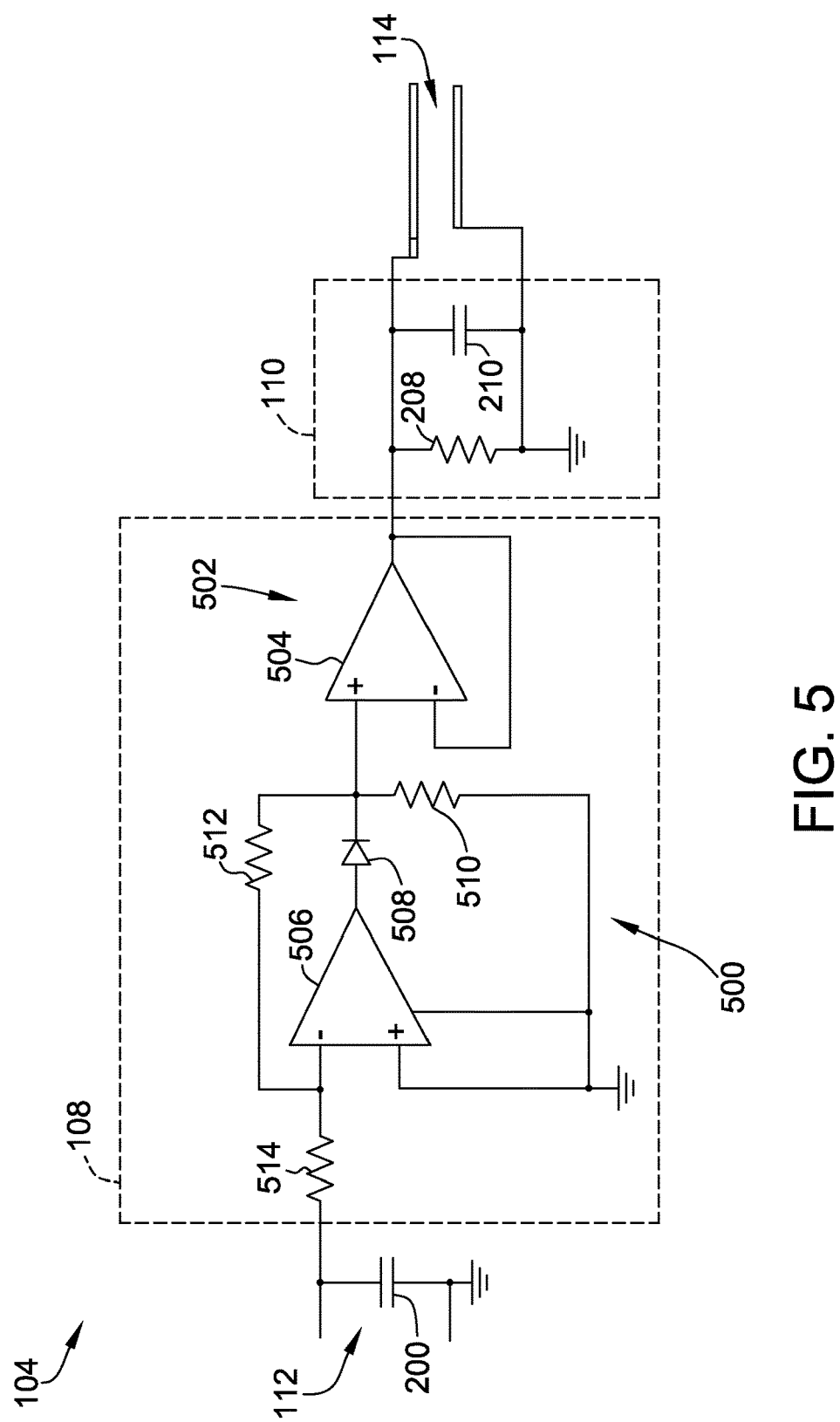
FIG. 5 is a simplified schematic of another example signal detector for use in the detection assembly shown in FIG. 1.

Now leaving the specific example, FIG. 5 is a schematic diagram of an exemplary embodiment of signal detector 104 with an active rectifier circuit 108 and passive peak detector circuit 110. A sensor signal is input to signal detector 104 through feed-through capacitor 200 at input 112. Active rectifier circuit 108 receives the sensor signal and outputs a rectified signal to passive peak detector circuit 110. Passive peak detector circuit 110 transmits an output signal through output 114. Passive peak detector circuit includes resistor 208 and capacitor 210. Active rectifier circuit 108 includes full wave rectifier 500 and buffer 502. Buffer 502 is a unity gain buffer amplifier including operational amplifier 504. Buffer 502 has a high impedance input for receiving the output of full wave rectifier 500 and a low impedance output to provide the output signal of full wave rectifier 500 to peak detector circuit 110 with minimal losses. Full wave rectifier 500 includes operational amplifier 506, diode 508, and resistors 510, 512, and 514. When an input signal, such as the sensor signal, is less than zero, full wave rectifier 500 operates as an inverting amplifier with a gain of:

$$\text{Inverting gain} = -\frac{R2}{R1} \qquad (1)$$

where R2 is the resistance of resistor 512 and R1 is the resistance of resistor 514. When the input signal is greater than zero, the full wave rectifier has a noninverting gain of:

$$\text{Noninverting Gain} = \frac{1}{1+\left(\frac{R1+R2}{R3}\right)} \qquad (2)$$

where R3 is the resistance of resistor 510. The resistance of resistors 510, 512, and 514 is selected so that the inverting gain and the non-inverting gain are substantially equal to maintain the same proportionality of the output signal for both positive and negative input signals. In one example implementation, resistor 510 has a resistance of 15 kΩ, resistor 512 has a resistance of 5 kΩ, and resistor 514 has a resistance of 10 kΩ. Thus, according to equations (1) and (2), the example active rectifier circuit 108 has an inverting and non-inverting gain of one half Other implementations may be configured to have any other suitable gain, including a gain greater than one. In one example implementation, operational amplifiers 504 and 506 are the two operational amplifiers of a LM358 dual operational amplifier and diode 508 is a 1N4148 diode. In other implementations, any other suitable diode and/or operational amplifiers, including two different operational amplifiers, may be used. It should be understood that active versions of rectifier circuit 108 are not limited to the exemplary rectifier circuit illustrated in FIG. 5 and rectifier circuit 108 may be any suitable active or passive rectifier circuit capable of operating as generally described herein. For example, active rectifier circuit 108 may include a synchronous rectifier, an active half wave rectifier, a dual operation amplifier rectifier, a single operation amplifier (whether full wave or half wave) with or without a buffer, etc.

The output of active rectifier circuit 108 is provided to passive peak detector circuit 110, which operates as described above. In other embodiments, peak detector circuit 110 is an active peak detector circuit 110 including one or more operation amplifiers. Active peak detector circuits are well known to those of ordinary skill in the art and will not be further described herein.

Figure 6:
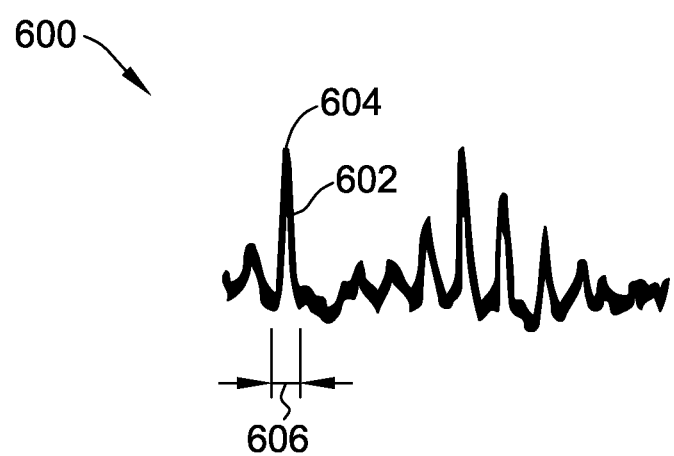
FIG. 6 is a graphical representation of an example neural signal that may be detected by the detection assembly shown in FIG. 1.
Figure 7:
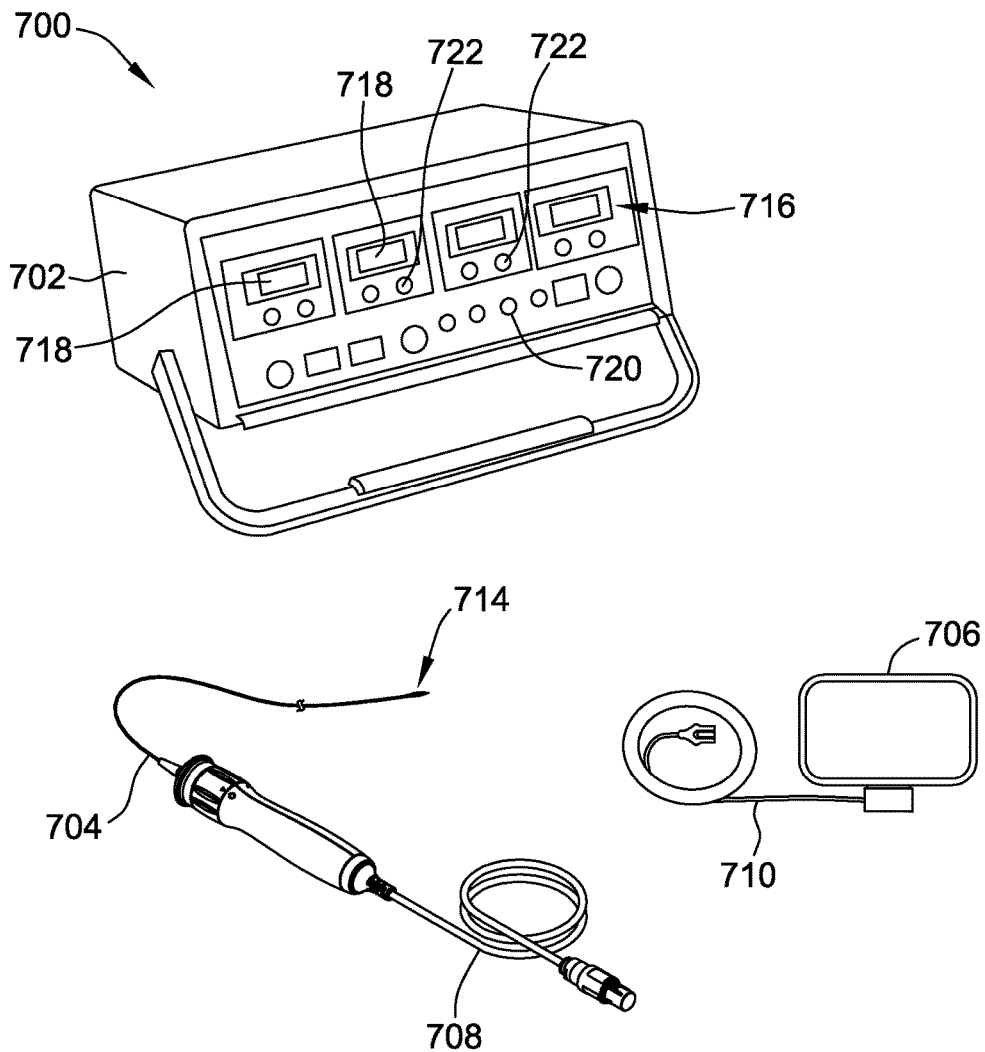
FIG. 7 is an isometric view of one embodiment of an ablation system including a generator, a catheter, and a return electrode.

Detection assembly 100 may be included in and/or used in conjunction with any system in which relatively high frequency signals are to be sensed. In some exemplary systems, the detection assembly 100 is used to detect neural signals. FIG. 6 shows an example of neural signals 600. In particular, the neural signals 600 are muscle sympathetic nerve activity accessed in the peroneal nerve using microneurography. Each signal has a peak magnitude and a duration. For example, signal 602 has a peak magnitude 604, and a duration 606. The specific magnitude and duration can vary among different nerves, different types of nerves, and among different firings of a single nerve. In general, duration 606 of a nerve signal is relatively short, e.g., one to three milliseconds. As can be seen in FIG. 6, neural signals 600 have varying magnitudes and generally occur stochastically and non-synchronized. Moreover, the rate of nerve firings can vary between five and five thousand firings per second. Because of the high frequency of the nerve signals, accurate detection and reproduction of neural signals, such as neural signals 600, typically requires a relatively high sampling rate, e.g., greater than four kHz. For some uses as described herein, however, reproduction of all of the details of a neural signal is not needed and/or desired. In such instances, detection assembly 100 may be utilized to convert the high frequency, time varying neural signals to lower frequency output signals that indicate the peak magnitude(s) of the neural signals. Thus, controller 106 may utilize a lower sampling rate to gain information about the neural signals than would be required to accurately sample the unmodified neural signals.

For example, in some embodiments, detection assembly 100 is included in or on, or used in conjunction with, a spinal cord stimulator (SCS). SCS pulse generators apply stimulation to the spinal cord to provide many potential benefits. Detection assembly 100 may be used to sense neural firing patterns along a patient's spinal cord and peripheral nerves for use as feedback for the SCS system, to study the efficacy of treatment, and/or for any other suitable use.

In other embodiments, the detection assembly is incorporated in or on, or used in conjunction with, a cardiac rhythm medical device (CRMD). Detection assembly 100 may be used to detect cardiac neural signals, which may be used, for example, to determine the response to neuro-stimulations. In still other embodiments, detection assembly 100 may be incorporated within and/or used in conjunction with an ablation system, including both cardiac ablations systems and renal ablation systems. More specifically, in some embodiments, detection system 100 is used to detect neural signals in connection with a neural ablation system. The detection system may be used to detect the magnitude of neural signals before an ablation and after an ablation to facilitate determining the effectiveness of the ablation, and hence the overall procedure. An exemplary ablation system incorporating detection system 100 is described below. It should be understood, however, that the detection system described above may be used with any other suitable system, including SCS systems, other ablation systems, CRMDs, etc. In many embodiments, nerve sensing electrodes including the neural signal detectors described herein may be located close to ablation electrodes or pacing electrodes without interference.

An exemplary ablation system 700 including detection system 100 will now be described with reference to FIGS. 7-10. Ablation system 700 includes an generator 702, multi-electrode ablation catheter 704, and return electrode 706. Ablation catheter 704 is removably coupled to generator 702 by cable 708. Return electrode 706 is removably coupled to generator 702 by cable 710. In use, return electrode 706 is placed externally against a patient's body and catheter 704 is inserted into the patient's body. Generally, generator 702 outputs radio frequency (RF) energy to catheter 704 through cable 708. The RF energy leaves catheter 704 through a plurality of electrodes 712 (shown in FIG. 8) located at distal end 714 of catheter 704. The RF energy travels through the patient's body to return electrode 706. The dissipation of the RF energy in the body increases the temperature near the electrodes, thereby permitting ablation to occur. In the exemplary embodiment set forth herein, ablation system 700 is a renal ablation system suitable for use in performing renal denervation procedures. It is understood, however, that the ablation system may be used for other treatments, including cardiac ablation treatments, without departing from the scope of the present disclosure.

Generator 702 includes a user interface (UI) portion 716 for displaying information and notifications to an operator and receiving input from the user. Display devices 718 visually display information, such as measured temperatures, power output of the generator, temperature thresholds, cycle time, etc., and/or notifications to the user. Display devices 718 may include a vacuum fluorescent display (VFD), one or more light-emitting diodes (LEDs), liquid crystal displays (LCDs), cathode ray tubes (CRT), plasma displays, and/or any suitable visual output device capable of displaying graphical data and/or text to a user. Indicators 720 provide visual notifications and alerts to the user. In other embodiments, one or more of indicators 720 provide audible notifications and/or alerts to the user. In the illustrated embodiment, indicators 720 are lights, such as light emitting diodes, incandescent lamps, etc. Indicators 720 may be turned on or off, for example, to indicate whether or not generator 702 is receiving power, whether or not catheter 704 is connected, whether or not catheter 704 (or all electrodes 712) is functioning properly, etc. Moreover, indicators 720 may indicate a quality or degree of a feature or component of ablation system 700, such as by changing color, changing intensity, and/or changing the number of indicators 720 that are turned on. Thus, for example, an indicator 720 may change color to represent a unitless notification of the quality of the contact between one or more of electrodes 712 and an artery wall, or to indicate a comparison between pre-ablation neural signals and post-ablation neural signals. UI portion 716 includes inputs 722, e.g., buttons, keys, knobs, etc., for receiving commands and/or requests from a user.

Figure 8:
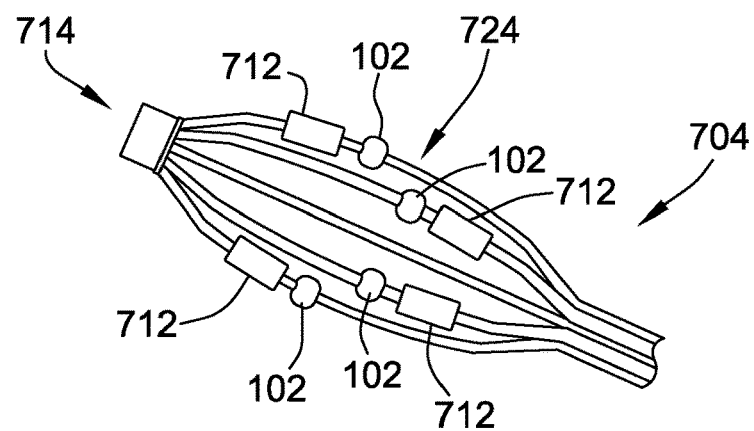
FIG. 8 is a partial view of a distal end of the catheter shown in FIG. 7.

As shown in FIG. 8, multiple electrodes 712 may be disposed on basket 724 located at distal end 714 of catheter 704. In the illustrated embodiment, basket 724 is an expandable basket that may be expanded and collapsed by an operator of ablation system 700 to position electrodes 712 against, for example, an artery wall. In the illustrated embodiment, catheter 704 includes four electrodes 712. In other embodiments, catheter 704 may include at least two, but other than four, electrodes 712. A thermocouple (not shown, also referred to herein as a temperature sensor) is attached to each electrode 712 to provide temperature readings of electrode 712. Catheter 704 also contains a thermistor (not shown) and a 1-Wire EEPROM. Generator 702 uses the thermistor for measuring ambient temperature and performing cold-junction compensation on the thermocouples. The EEPROM contains a unique ID which allows generator 702 to reject devices not manufactured specifically for use with generator 702. Generator 702 also maintains usage data on the EEPROM in order to enforce maximum operation limits for catheter 704.

Figure 9:
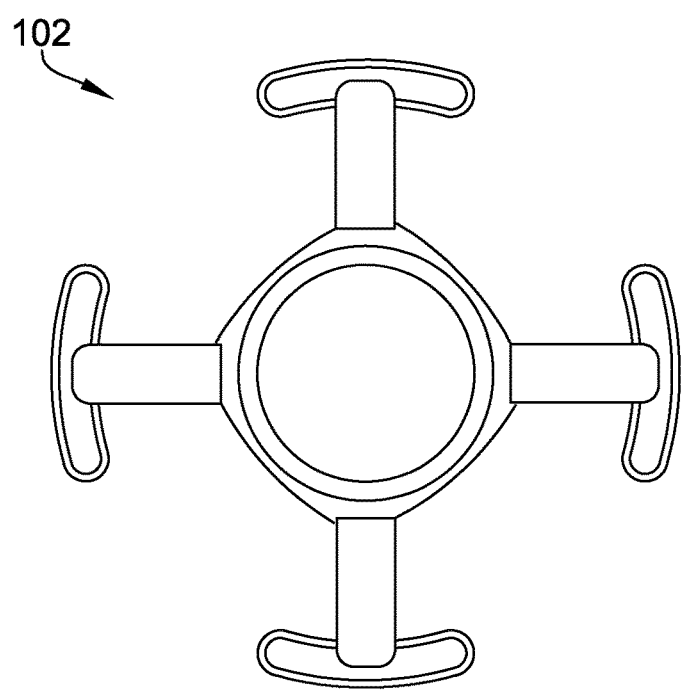
FIG. 9 is a plan view of an example neural sensor for use in the system shown in FIG. 7.
Figure 10:
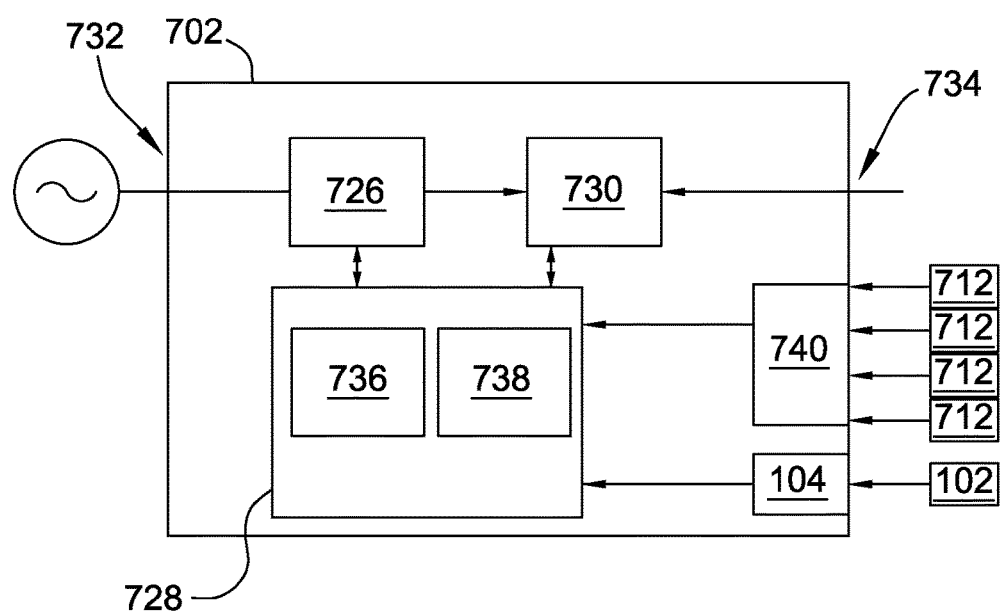
FIG. 10 is a schematic block diagram of a controller for use in the generator shown in FIG. 7.

In the illustrated embodiment shown in FIG. 8, four sensors 102 are disposed on basket 724 near electrodes 712. Sensors 102 may be any sensors suitable for sensing neural firings occurring near sensors 102 and generating a sensor signal representative of the sensed neural firing. In the illustrated embodiment, sensors 102 are non-contact neural sensors; that is, neural sensors that do not require direct contact with a nerve to sense a reading or firing of the nerve. Of course, other sensors that contact the nerve directly are within the scope of the present disclosure. More specifically, as shown in FIG. 9, illustrated sensors 102 are split ring neural sensors. A split ring sensor is a generally toroidal, or ring, shape split into between two and four segments. In the illustrated embodiment shown in FIG. 9, sensor 102 is a four segment split ring. Any two of the segments of the four segment split ring may be utilized as a bipolar sensor. In the exemplary embodiment, signal detector 104 and controller 106 are located within generator 702 (as shown in FIG. 10 and discussed below), and sensor signals are transmitted, such as through a conductor within catheter 704, from sensors 102 to signal detector 104 within generator 702. In other embodiments, signal detector 104 is integrated within catheter 704, and signal detector 104 output signals are transmitted, such as through one or more conductors within catheter 704, from signal detector 104 to controller 106. In still other embodiments, signal detector 104 and controller 106 are incorporated within catheter 704.

Referring now to FIG. 10, generator 702 includes a power supply 726, a controller 728, and an RF output circuit 730. A multiplexer 740 receives inputs from electrodes 712. Signal detector 104 receives sensor signals from sensors 102 and provides its output signal(s) to controller 728. Power supply 726 receives AC power via an input 732 and converts the received power to a DC power output. The DC power output is provided to the RF output circuit 730 that outputs RF power to catheter 704, and more specifically to electrodes 712, via output 734. Controller 728 is coupled to and controls operation of power supply 726 and RF output circuit 730. Controller 728 controls when and to which electrodes 712 the RF output circuit 730 couples its RF power output. In other embodiments, one or both of the RF output circuit 730 and power supply 726 includes its own controller configured to control operation in response to commands from controller 728. In the illustrated embodiment, controller 728 also functions as controller 106. In other embodiments, controller 106 is separate from controller 728.

Controller 728 includes processor 736 and memory device 738 coupled to processor 736. The term "processor" refers herein generally to any programmable system including systems and microcontrollers, reduced instruction set circuits (RISC), application specific integrated circuits (ASIC), programmable logic circuits, field programmable gate array (FPGA), gate array logic (GAL), programmable array logic (PAL), digital signal processor (DSP), and any other circuit or processor capable of executing the functions described herein. The above examples are exemplary only, and thus are not intended to limit in any way the definition and/or meaning of the term "processor." Moreover, although a single processor is illustrated in FIG. 10, processor 736 may include more than one processor and the actions described herein may be shared by more than one processor.

Memory device 738 stores program code and instructions, executable by processor 736. When executed by processor 736, the program code and instructions cause processor 736 to operate as described herein. Memory device 738 may include, but is not limited to only include, non-volatile RAM (NVRAM), magnetic RAM (MRAM), ferroelectric RAM (FeRAM), read only memory (ROM), flash memory and/or Electrically Erasable Programmable Read Only Memory (EEPROM). Any other suitable magnetic, optical and/or semiconductor memory, by itself or in combination with other forms of memory, may be included in memory device 738. Memory device 738 may also be, or include, a detachable or removable memory, including, but not limited to, a suitable cartridge, disk, CD ROM, DVD or USB memory. Although illustrated separately from processor 736, memory device 738 may be integrated with processor 736.

In operation, when catheter 704 is positioned at a location for an ablation, each sensor 102 detects neural signals having neural activity near itself. These pre-ablation neural signals are transmitted to signal detector 104, which generates pre-ablation output signals having magnitudes proportional to the peak magnitudes of detected neural signals and a frequency less than the frequency of the original neural signals. After an ablation has occurred at a location, post-ablation neural signals are sensed and transmitted from sensors 102 to signal detector 104. Signal detector 104 generates post-ablation output signals having magnitudes proportional to the peak magnitudes of detected post-ablation neural signals and a frequency less than the frequency of the post-ablation neural signals. Controller 728 samples the pre-ablation and post-ablation output signals at a sampling frequency that is less than the twice the frequency of the pre-ablation and post-ablation neural signals. In other embodiments, controller 728 samples the pre-ablation and post-ablation output signals at a sampling frequency that is less than the frequency of the pre-ablation and post-ablation neural signals. In some embodiments, the controller samples the pre-ablation and post-ablation output signals at a sampling frequency of about 512 Hz. In other embodiments, the controller samples the pre-ablation and post-ablation output signals at a sampling frequency of about 200 Hz. In some embodiments, the controller samples the pre-ablation and post-ablation output signals at a sampling frequency selected as a function of the time constant of signal detector 104. After sampling the pre-ablation and/or post-ablation output signals, controller 728 may store the sampled signals, such as in memory device 738.

Controller 728 determines a difference between the magnitudes of the pre-ablation output signals and the post-ablation output signals and generates an indication of the determined difference. The indication may be a visual or audible indication. For example, controller 728 may display a value of the difference, e.g., an average percentage difference, on display device 718, may display an indication of the difference using indicators 720, may audibly announce an indication of the difference, etc. In some embodiments, controller 728 compares the determined difference to a predetermined threshold value and generates an indication of whether or not the difference exceeds the threshold value. Thus, for example, if a 75% decrease in the magnitude of the neural signals is desired for an ablation to be considered successful, controller 728 may determine whether or not the post-ablation output signals indicate a 75% decrease from the pre-ablation output signals. If controller 728 determines that the threshold has been exceeded, controller 728 may provide an indication, whether audible or visual, that the ablation was successful. In other embodiments, controller 728 provides an indication when the ablation is unsuccessful.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above without departing from the scope of the disclosure, it is intended that all matter contained in the above description and shown in the accompanying drawings shall be interpreted as illustrative and not in a limiting sense.

What is claimed is:

1. A neural signal detector comprising:
    a rectifier circuit configured to receive a time varying neural signal having a first frequency from a neural sensor and output a rectified signal corresponding to the received signal; and
    a peak detector circuit operatively connected to the rectifier circuit to receive the rectified signal and configured to provide an output signal comprising a positive square wave having a peak magnitude proportional to a peak magnitude of the rectified signal and having a second frequency less than the first frequency of the neural signal.

2. The neural signal detector of claim 1 wherein the rectifier circuit comprises a passive rectifier circuit.

3. The neural signal detector of claim 2 wherein the passive rectifier circuit includes a diode.

4. The neural signal detector of claim 3 wherein the diode is a Schottky diode.

5. The neural signal detector of claim 1 wherein the rectifier circuit comprises an active rectifier circuit.

6. The neural signal detector of claim 5 wherein the active rectifier circuit comprises a full wave active rectifier.

7. The neural signal detector of claim 1 wherein the peak detector circuit comprises a passive peak detector circuit.

8. The neural signal detector of claim 7 wherein the passive peak detector circuit comprises a resistor coupled in parallel with a capacitor.

9. The neural signal detector of claim 1 wherein the peak detector circuit is an active peak detector circuit.

10. The neural signal detector of claim 9 wherein the active peak detector circuit comprises at least one operational amplifier.

11. A detection assembly comprising:
    a signal detector comprising:
        a rectifier circuit configured to receive a sensor signal having a peak magnitude and a first frequency; and
        a peak detector circuit configured to generate an output signal comprising a positive square wave having a magnitude proportional to the peak magnitude of the sensor signal and having a second frequency less than the first frequency of the sensor signal.

12. The detection assembly of claim 11 further comprising a sensor operatively coupled to the signal detector and operable to generate the sensor signal.

13. The detection assembly of claim 12 wherein the sensor is a neural sensor operable to generate the sensor signal in response to a neural signal proximate the neural sensor.

14. The detection assembly of claim 11 further comprising a controller operatively coupled to the signal detector to receive the output signal.

15. The detection assembly of claim 14 wherein the controller is operable to sample the output signal at a maximum sampling rate less than the first frequency.

16. The detection assembly of claim 14 wherein the controller is operable to sample the output signal at a maximum sampling rate less than twice the first frequency.

* * * * *